US00PP09247P

United States Patent [19]

Egger

[11] Patent Number: Plant 9,247

[45] Date of Patent: Aug. 15, 1995

[54] *LONGIFLORUM*×ASIATIC HYBRID LILY PLANT NAMED 'CEB BEAUTY'

[75] Inventor: Donald L. Egger, Aurora, Oreg.

[73] Assignee: Cebeco Lilies, Inc., Aurora, Oreg.

[21] Appl. No.: 333,493

[22] Filed: Nov. 2, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Klarquist Sparkman Campbell Leigh & Whinston

[57] ABSTRACT

A new and distinct lily hybrid named 'Ceb Beauty' characterized by numerous upright, large, vibrant orange colored flowers on tall, strong stems excellent for cut flower production.

1 Drawing Sheet

BACKGROUND OF THE INVENTION

The present invention comprises a new and distinct cultivar of lily hybrid, referred to commercially as a *longiflorum*-Asiatic Lily Hybrid, referred to by the cultivar name 'Ceb Beauty'.

This invention is the product of a controlled breeding program in Aurora, Or. The seed parent was GH 485, a proprietary non-released plant. The pollen parent was PATM 1, another proprietary non-released plant.

The *longiflorum*-Asiatic cross is relatively new to the trade. This type of cross was originally made to create colored *Lilium longiflorum* hybrids. Instead, due to the difficulty in crossing back to *L. longiflorum,* the plants that were developed had to be crossed with Asiatic lilies. As such, the results look more like Asiatic lilies. The resulting hybrids often have several advantages, not necessarily in combination, over an Asiatic lily: (1) often larger flowers; (2) often larger, waxier leaves; (3) hybrid vigor; (4) lower susceptibility to scorch; (5) excellent flower texture and substance; (6) more virus resistance; (7) new and clearer colors; and (8) stronger, sturdier stems.

This invention has not been observed under all possible environmental conditions. The phenotype may vary significantly with variations in environment such as temperature, light intensity, and day length, without, however, any variation in genotype. The following traits have been repeatedly observed in asexually propagated progeny and are determined to be the basic characteristics of this invention which in combination distinguish this lily as a new and distinct cultivar: (1) numerous large, upright flowers of a vibrant orange with very few spots; (2) beautiful orange buds; (3) tall, vigorous, uniform strong stems; (4) excellent vase life; (5) early bloom time; and (6) good bud count. Bulbs of this plant may be precooled and forced out of season for very uniform cut flower production.

To the inventor's knowledge, there are no other *longiflorum*-Asiatic lily hybrids with this color flower suitable for cut flower forcing on the market. Compared to my other new cultivar 'Ceb Magic', 'Ceb Beauty' has taller stems, more flowers per stem, and fewer spots.

Asexual reproduction of this new variety has been initially and subsequently accomplished at Cebeco Lilies, Inc. in Aurora, Or., by scaling and tissue culture. The resulting plants have shown that the above-mentioned unique features are stable and reproduce true to type in each successive propagation.

Figure 2:
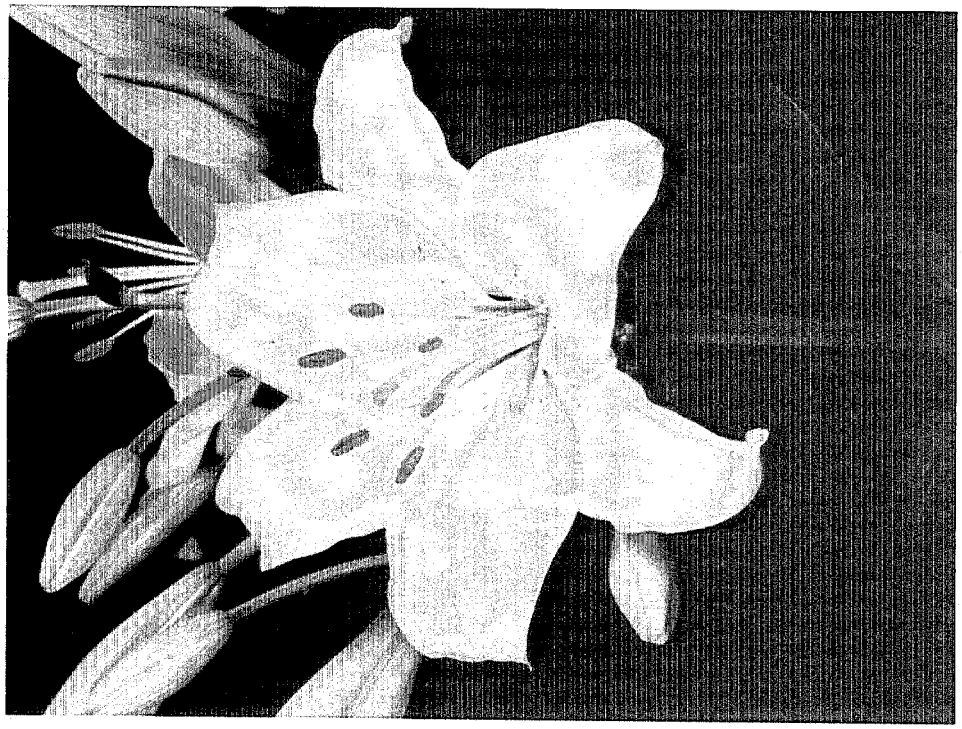
FIG. 2 is a close-up photograph which illustrates in greater detail a single flower of the new plant.
Figure 1:
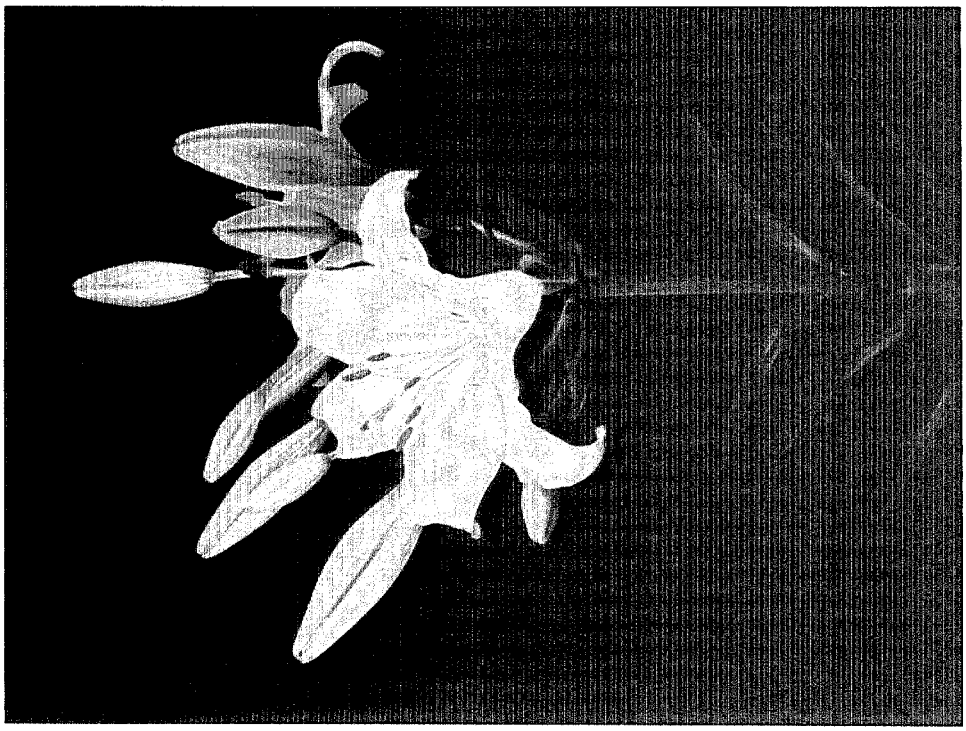
FIG. 1 is a photograph showing the 'Ceb Beauty' lily.

The photographs of the drawing were taken in August 1993 in a studio and illustrate the typical flower and foliage form, with color being as true as is reasonably possible in this type of color photograph.

DETAILED DESCRIPTION

The following is a detailed description of the invention based on plants produced under commercial practices in the Cebeco Lilies, Inc. greenhouses in Aurora, Or. in July 1993. Color references are made to The Royal Horticultural Society Colour Chart (RHS), except where the context indicates a term having its ordinary dictionary meaning.

THE PLANT

Origin: Seedling.

Parentage:

*Seed parent.*—GH 485.

*Pollen parent.*—PATM 1.

Commercial classification: Upright *longiflorum*-Asiatic hybrid, cut flower type.

Classification: Division VIII, according to the Horticultural Classification of Lilies by The Royal Horticultural Society of London.

Form: Single erect stem bearing terminal cluster of flowers. Stem mottled with Grayed Purple Group 187A.

Height: About 120 cm. from the top of the soil to the top of the flowers from bulbs of 12 cm. in circumference.

Growth habit: Vigorous, upright and rigid.

Foliage:

*Arrangement.*—Spiral.

*Quantity.*—Average.

*Leaf size.*—About 13 cm. long and 13 mm. wide.

*Leaf shape.*—Linear-lanceolate with entire margins. Leaf base is pubescent.

*Texture.*—Leathery.

*Aspect.*—Glossy.

*Color.*—Dark green on both sides, closest to 147A.

Bulbs:

*Size.*—Variable, ranging to about 12–14 cm. in circumference as used commercially.

*Color.*—White.

THE BUD

Size: Large, to about 9.5 cm. long and 3.4 cm. wide just prior to opening.

Shape: Ovoid with an obtuse tip.

Rate of opening: The mature bud opens slowly in response to light.

Color: Orange. Orange-Red Group 30C-D.

THE FLOWER

Blooming habit: Annually, once and early season.

Days to bloom: Flowers approximately 76 days after spring greenhouse planting under typical commercial flower forcing conditions of 15° Celsius night time temperatures.

Flower size: Large.

*Diameter.*—About 14.5 cm.

*Depth.*—About 8 cm.

Borne: In a modified raceme of from about 11 to 16 flowers from bulbs 16 cm. in circumference.

Shape: When the flower first opens it is bowl-shaped. Later, the shape flattens out and the tepals reflex sharply at the tips.

Tepalage:

*Number.*—Six.

*Arrangement.*—Imbricated.

*Shape.*—Ovate.

*Texture.*—Leathery, spongy.

*Aspect.*—Satiny.

*Size.*—Length: About 10 cm. Width: Inner tepals — about 50 mm. Outer tepals — about 40 mm. Depth of imbrication. —About 20 mm.

*Nectary.*—About 3 cm. long; red orange; white papillose; with the channels close together.

*Projections.*—None.

*Spots.*—Few (5–15 per tepal), small, on the bottom ⅓ of the tepals. Grayed-Purple 187B.

*Blush.*—None.

*Color.*—Topside: Vibrant Orange. Orange Group 28B Bottomside: Orange Group 25C with the edges darker, Orange Group 28B.

*Discoloration.*—Slight discoloration with age.

*Fragrance.*—Slight.

*Lasting quality.*—Excellent.

Pedicel:

*Length.*—Variable. From 5–9 cm.

*Color.*—Yellow-green mottled with maroon spots.

*Orientation.*—Ascending upwardly from about 45°–70° from the horizontal.

THE REPRODUCTIVE ORGANS

Stamens:

*Number.*—Six, typical of the genus Lilium.

*Anthers before dehiscence.*—Size: About 2 cm. Color: Tan. Grayed-Orange Group 166D-167D.

*Filaments.*—Length: About 7.5 cm. Color: Light orange. Orange Group 24D at top to a near white, Orange Group 27D at base.

*Pollen.*—Color: Bright red orange. Orange Group 32A.

Pistil:

*Number.*—One.

*Style.*—Length: About 7.3 cm. Color: Orange Group 25C.

*Stigma.*—Color: Light orange, Orange Group 25D.

THE FRUIT

Fertility: The fruit is infertile.

Shape: Ovoid.

Color at maturity: Soft Brown.

I claim:

1. A new and distinct cultivar of *longiflorum*-Asiatic hybrid lily plant substantially as herein shown and described.

* * * * *